United States Patent [19]

Matusewicz et al.

[11] Patent Number: 5,337,426
[45] Date of Patent: Aug. 16, 1994

[54] DISPOSABLE SAMPLE COLLECTION DEVICE

[75] Inventors: Richard S. Matusewicz, San Jose; Josefina T. Baker, Cupertino, both of Calif.

[73] Assignee: Beckman Instruments, Inc., Fullerton, Calif.

[21] Appl. No.: 88,491

[22] Filed: Jul. 6, 1993

Related U.S. Application Data

[63] Continuation of Ser. No. 919,637, Jul. 24, 1992, abandoned, and a continuation-in-part of Ser. No. 616,491, Nov. 21, 1990, abandoned.

[51] Int. Cl.$^5$ .............................................. A47K 11/00
[52] U.S. Cl. .............................................. 4/661; 4/484
[58] Field of Search ......................... 4/245.1–245.9, 4/449, 452, 479, 484, 661, DIG. 18; 229/125.36; 158/154; 428/131, 134, 136

[56] References Cited

U.S. PATENT DOCUMENTS

| | | |
|---|---|---|
| D. 267,273 | 12/1982 | Paulin . |
| 772,425 | 10/1904 | Michaels ..................... 4/243 |
| 1,077,277 | 11/1923 | Holmes ..................... 4/243 |
| 1,377,791 | 5/1921 | Potschner ..................... 4/245.9 |
| 1,462,662 | 7/1923 | Scheaefer ..................... 4/243 |
| 1,505,067 | 8/1924 | Lahmer ..................... 4/243 |
| 1,673,622 | 6/1928 | Engalitcheff ..................... 4/245.9 |
| 1,744,300 | 1/1930 | Dewaide ..................... 4/243 |
| 1,961,195 | 6/1934 | Carruthers ..................... 4/242 X |
| 2,801,424 | 8/1957 | Mercer . |
| 2,840,826 | 7/1958 | Ebbesen et al. . |
| 2,944,725 | 7/1960 | Hayes ..................... 229/125.36 |
| 3,346,883 | 10/1967 | Ersek . |
| 3,466,145 | 9/1969 | Van Duyne . |
| 3,484,875 | 12/1969 | Eisenberg ..................... 4/484 |
| 3,531,298 | 9/1970 | Donahue ..................... 229/125.36 X |
| 3,540,433 | 11/1970 | Brockman ..................... 4/661 X |
| 3,571,817 | 3/1971 | Gosnell . |
| 3,588,921 | 6/1971 | Nagel . |
| 3,625,654 | 12/1971 | Van Duyne . |
| 3,654,638 | 4/1972 | Nye . |
| 3,754,287 | 8/1973 | Taylor . |
| 3,944,694 | 3/1976 | McQueary ..................... 428/131 |
| 4,101,279 | 7/1978 | Aslam . |
| 4,203,169 | 5/1980 | Dale . |
| 4,290,546 | 9/1981 | Kanaga et al. ..................... 229/125.36 |
| 4,309,782 | 1/1982 | Paulin . |
| 4,445,235 | 5/1984 | Slover et al. . |
| 4,521,520 | 6/1985 | Jacke . |
| 4,705,050 | 11/1987 | Markham . |
| 4,935,969 | 6/1990 | Farnsworth ..................... 4/484 |
| 4,975,990 | 12/1990 | Chan ..................... 4/243 |
| 5,155,871 | 10/1992 | Sams ..................... 4/484 |

FOREIGN PATENT DOCUMENTS

| | | |
|---|---|---|
| 1920231 | 12/1970 | Fed. Rep. of Germany ....... 4/245.1 |
| 297247 | 9/1928 | United Kingdom ..................... 4/243 |

OTHER PUBLICATIONS

"A Stool Collection Device: The First Step in Occult Blood Testing" (*Annals of Internal Medicine* [1988] 108:609–612).

"The First Step in Occult Blood Testing" (ABC Medical Enterprises, Rochester, Minnesota, Copyright 1990).

"SC–Tray Fact Sheet".

*Primary Examiner*—Charles E. Phillips
*Attorney, Agent, or Firm*—William H. May; Gary T. Hampson

[57] ABSTRACT

A specimen collection device including a sheet of flexible material and two generally parallel slits formed near opposite edges of the sheet. This sheet is preferably rectangular and is of sufficient dimensions such that the slits may receive a conventional toilet seat to suspend a central portion of the device under the seat within a toilet bowl. The central portion is adapted to receive a fecal specimen and the device and specimen may be easily disposed of.

10 Claims, 3 Drawing Sheets

DISPOSABLE SAMPLE COLLECTION DEVICE

This is a continuation of copending application Ser. No. 07/919,637 filed on Jul. 24, 1992 now abandoned, and a continuation-in-part of copending application Ser. No. 07/614,491 filed on Nov. 21, 1990 now abandoned.

FIELD OF THE INVENTION

The present invention relates generally to the field of sample collection and more particularly to fecal sample collection for use in the testing of fecal material for occult blood and other analytes.

BACKGROUND

Various specimen collection devices are known for assisting in the collection of stool specimens. The specimens are often collected so that samples can be removed from the specimens for later testing for fecal occult blood.

One such stool specimen collector is described in U.S. Pat. No. 4,445,235 which discloses a tray-type collector and a cradle-type collector. Both collectors are fastened to a toilet bowl or toilet seat by means of adhesive pads. Once the specimen is collected, however, these pads are often difficult to peal away from the toilet bowl or seat. If the cradle-type collector is to be disposed of by flushing it down the toilet, the adhesive pads can inadvertently adhere to the inner passageways of the toilet itself or to sewer pipes connected to the toilet, thereby clogging the toilet or sewer pipes. The adhesive pads may not be readily biodegradable, posing a further disposal problem. Both the tray-type and cradle-type collector disclosed in the 4,445,235 patent are complicated to manufacture, requiring assembly of several components which adds to the expense and bulk of the collectors.

Another device, available from Ability Building Center, Inc. (ABC) (Rochester, Minn. 55903) consists of a cardboard yoke and a flushable, detachable paper dish. The cardboard yoke receives the paper dish and may be affixed to the toilet bowl seat by means of adhesive tape. Although the paper dish is disposable in the toilet, it may be somewhat difficult and thus aesthetically unappealing for the person using the device to remove the dish from the yoke. This is because the dish is relatively small, requiring the user to manipulate the dish, such as by tearing the dish free or removing the dish from retaining tabs, in close proximity to the fecal specimen. Also, the cardboard yoke is not disposable in the toilet and thus presents an additional disposal problem. Furthermore, the ABC device suffers from the same drawback as the device disclosed in the 4,445,235 patent, namely, that the adhesive tape used to support the cardboard yoke is often difficult to remove from the toilet seat.

Yet another device is a collection tissue that is placed directly onto the surface of the water standing in the toilet bowl. Preferably, the sides of the bowl are wetted and the edges of the tissue are allowed to stick to the sides of the wetted bowl. Unfortunately, this collection tissue allows the fecal material to contact the toilet bowl water, allowing potential contamination and dilution that is generally undesirable when collecting samples that are tested for occult blood or other substances.

Thus, there is a need for an improved specimen collection device which overcomes the limitations noted above.

SUMMARY OF THE INVENTION

The present invention is directed to a disposable sample collection device. In one embodiment of the device, the device includes a sheet of flexible material. Two slits near opposite edges of the sheet are generally parallel to the first dimension and have lengths such that the toilet seat may be received within slots, that is, lengths greater than the width of a toilet seat but less than the first dimension. The device may be easily slipped over a toilet seat, providing a collection area generally in the interior portion of the sheet that is suspended above the surface of the water within the bowl. Once the specimen has been collected and a sample from the specimen taken for subsequent testing, the sheet may be easily torn free from the seat, lowering the remainder of the specimen and the sheet into the bowl for easy, sanitary disposal.

Another embodiment of the device includes a flexible sheet of material having a central portion which receives and supports the specimen as in the embodiment just described. Integrally formed parallel straps extend from opposite peripheral portions of the central portion. Suitable joining means, such as slits in the straps, are provided for removably forming the ends of opposite strap into a loop. The loops are correspondingly of sufficient size to receive a rim portion of a toilet seat. By placing this embodiment of the device beneath the lowered seat and forming the loops as just described, a convenient and sanitary collection device is formed. Once the samples are taken from a specimen collected by the device, the loops can be easily opened or the strap material simply torn to lower the remaining specimen and the collection device into the bowl for convenient disposal.

A further embodiment of the present invention includes a flexible sheet of material having a central portion which receives and supports the specimen. Two integrally formed arms extend from two opposite edges of the device. In the particular embodiment disclosed herein, the outer ends of the arms are pointed and in the shape of arrowheads. With the device placed on a toilet seat, the arms are placed around the opposite rims of the seat and the arrowhead-shaped ends of the arms are inserted through slits formed near the bases of the arms. The device is thus easily secured to the seat with the interior portion suspended above the surface of the water within the toilet bowl. After samples are taken from a specimen collected by the device, the device can be easily freed from the toilet seat by pulling or tearing the arrowhead-shaped ends from the slits and the device with the remaining specimen can be conveniently lowered into the toilet bowl for disposal.

Thus, the embodiments of the present invention provide for easy, clean and inexpensive specimen collection, in the form of readily disposable devices that are easily manufactured and are similarly easy to provide to patients for sample and specimen collection. The devices may be readily fully biodegradable.

DETAILED DESCRIPTION

Figure 1:
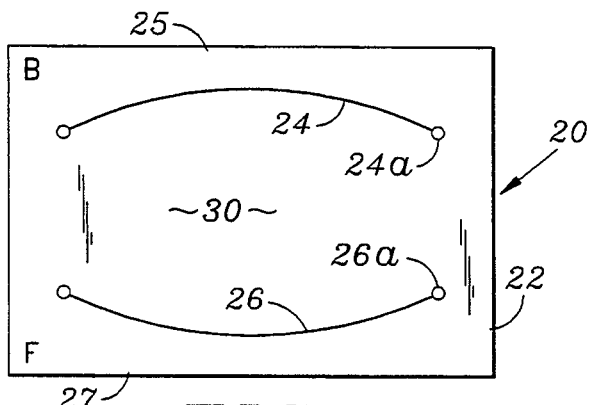
FIG. 1 is a top view of the device in accordance with the present invention.
Figure 2:
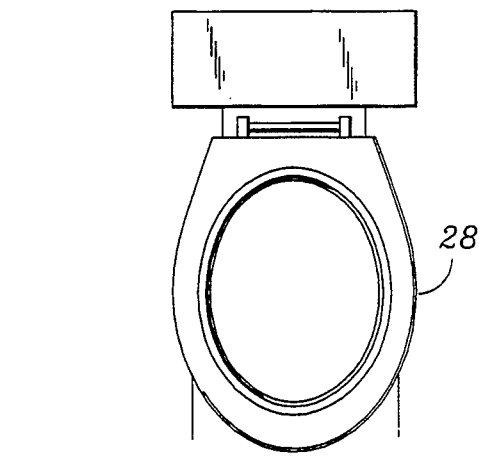
FIG. 2 is a top view of the device of FIG. 1 prepared for installation on a toilet seat.
Figure 3:
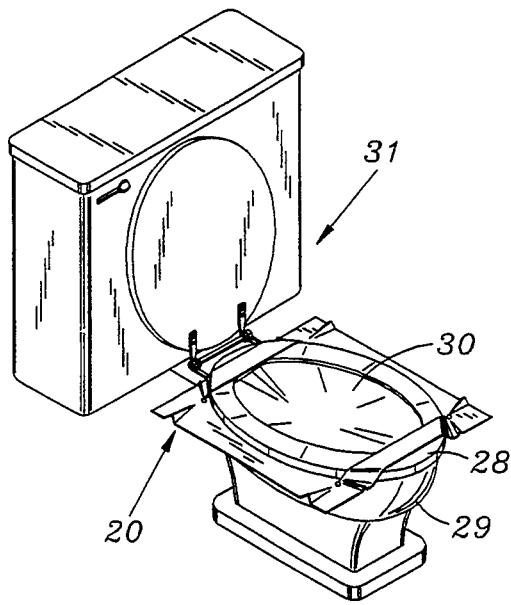
FIG. 3 shows the device of FIG. 1 installed on the seat of FIG. 2.
Figure 4:
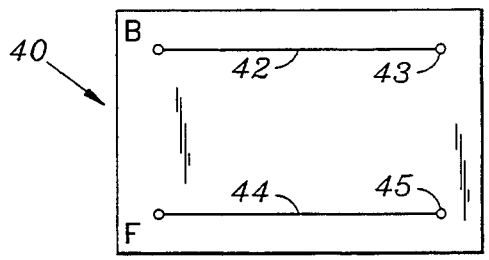
FIGS. 4–10 are alternative embodiments of the device of FIG. 1, illustrating various sheet configurations and slit shapes.

With references to FIGS. 1–3, a device 20 in accordance with the present invention includes a sheet 22 of flexible biodegradable material. The sheet 22 is rectangular in overall shape and is preferably formed from a single or multi-layered paper-like material such as type #8999 or type #611 available from the Scientific Specialties Group of Ahlstrom Filtration, Mount Holly Springs, Pa. Particularly with respect to these two examples of materials, both are tissue-like cellulose papers commonly sold for filtration purposes and are accordingly lightweight, non-rigid materials. For example, the type 8999 material is specified as 0.002 inch thick with a weight of five pounds per ream (500 sheets, 20 inches by 20 inches), and the type 611 material is specified as 0.0055 inches thick with a weight of 16 pounds per ream. Two generally parallel slits 24, 26 are formed in the sheet 22 parallel to the longer dimension of the device 20, defining straps 25, 27. The slits 24 and 26 each include stress distribution end eyes or holes 24a, 26a that serve to distribute or relieve stress at the ends of the slits 24 and 26 to help prevent ripping of the device material. As illustrated in the FIG. 1, the slits 24, 26 are near the respective parallel edges of the sheet 22 and are slightly curved outwardly from each other toward the edges. The letters "F" and "B" in FIG. 1, as well as elsewhere throughout the Figures, designates Front edge and Back edge, respectively, of the illustrated devices as such devices are positioned for installation onto and installed onto a toilet seat as, for example, shown in FIGS. 2 and 3.

The sheet 22 and slits 24, 26 are dimensioned to fit over a conventional toilet seat 28 as illustrated in FIGS. 2 and 3. To place the device 20 onto the toilet seat 28, the seat 28 is raised slightly. A central portion 30 of the device 20 is displaced with respect to the straps 25, 27. The device 20 is then slipped over the seat 28 with the straps 25, 27 on the upper side of the seat 28 and the central portion 30 on the lower side of the seat 28. The seat 28 is lowered to rest against the rim of the bowl 29. The patient utilizes toilet 31 in a usual fashion, depositing a fecal specimen generally upon the central portion 30 of the device 20. The patient may then remove several samples from the specimen for use, for example, on HEMOCCULT ® brand fecal occult blood test slides available from SmithKline Diagnostics, Inc., San Jose, Calif. 95134.

Once the samples have been collected, the straps 25, 27 can be easily torn and the device 22 lowered into the bowl 29. The toilet 31 is flushed as usual to cleanly and easily dispose of the fecal sample and the device 20.

It is apparent that the overall longer dimension of the device 20 as illustrated in FIG. 1 is longer than the corresponding width of the seat 28. The slits 24, 26 are also longer than the corresponding width of the seat 28, but less than the overall longer dimension of the device 20, so that the device 20 is easily installed over the seat 28. With the device 20 so installed, the central portion 30 hangs naturally below the seat 28 but above the surface of the water standing within the bowl 29. Advantageously, device 20 requires no adhesive strips or pads to secure the device 20 to the seat 28. Also, the device 20 is formed inexpensively from a single sheet of biodegradable paper or paper-like material, readily disposable in the toilet 31 yet which is easily and readily manufacturable. The device 20 may be supplied to the patient in a convenient, neatly folded, thin package easily suited for direct distribution. This advantage is particularly important when the device 20 is used for fecal occult blood screening programs where the device 20 as well as an occult blood test slide is distributed to a relatively large population and thus cost, ease of use and disposability are important concerns.

Figure 6:
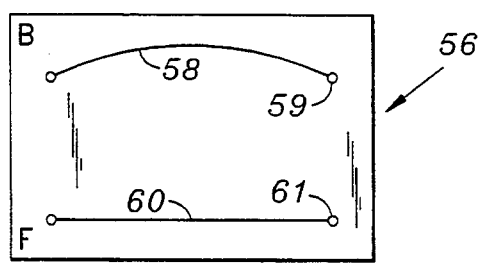
Figure 5:
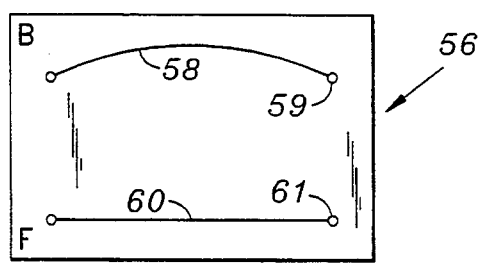

As alternatives to the embodiment of FIG. 1, the slits 24, 26 may be straight and/or curved inwardly. For example, with reference to FIGS. 4–10, a device 40 is similar to the device 20 but includes straight slits 42, 44 parallel to the respective edges of the device 40, and stress distribution end eyes or holes 43, 45. In FIG. 5, a device 46 includes slits 48, 50 and stress distribution end eyes or holes 49, 51. The slits 48, 50 are curved away from the respective parallel edges of the device 46 and towards each other, defining a narrowed central portion 52. A device 56 as seen in FIG. 6 includes a back slit 58 curved towards the other edge of the device 56, a straight front slit 60, and stress distribution end eyes or holes 59, 61.

Figure 7:
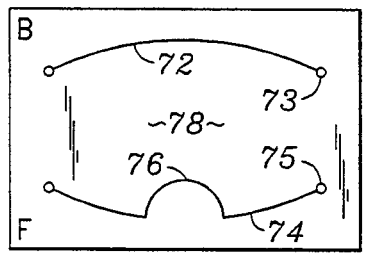
Figure 8:
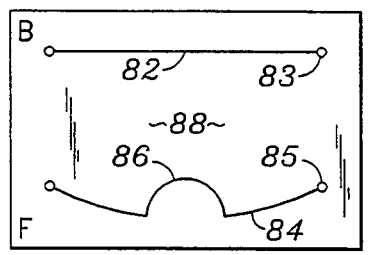

FIG. 7 illustrates a device 70 having a curved back slit 72 and stress distribution end eyes or holes 73, similar to the slit 24 and holes 24a. A front slit 74 includes stress distribution end eyes or holes 75 and a semicircular portion 76 directed towards the back slit 72. The semicircular portion 76 is approximately midway between the ends of the slit 74. Similarly, a device 80 as illustrated in FIG. 8 includes a straight back slit 82 and end eyes or holes 83 similar to the slit 42 and holes 43, and a curved front slit 84 with end eyes or holes 85 and a semicircular portion 86 similar to the slit 74, holes 75, and portion 76 of the device 70. The semicircular portions 76, 86 define a portion of central portions 78, 88 of the devices 70, 80 which, when installed on a toilet seat, helps avoid the unwanted collection of urine on the central portions 78, 88.

Figure 9:
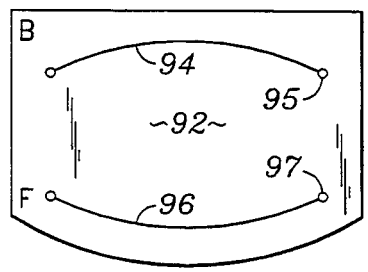
Figure 10:
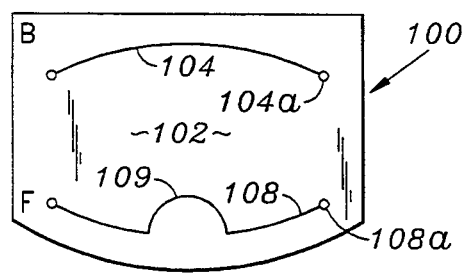

With reference to FIGS. 9 and 10, devices 90, 100 include sheets 92, 102 that have a straight back edge but an outwardly curved front edge as compared to the sheet 22. The device 90 includes curved slits 94, 96 and end eyes or holes 95, 97 similar to the slits 48, 50 and holes 49, 51 while the device 100 includes curved slits 104, 108, end eyes or holes 104a, 108a, and a semicircular portion 109 similar to the slits 72, 74, holes 73, 75, and the portion 76 illustrated in FIG. 7.

Figure 11:
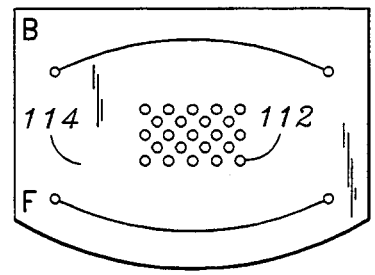
FIGS. 11 and 12 illustrate the devices of FIGS. 9 and 10, respectively, including drain holes.
Figure 12:
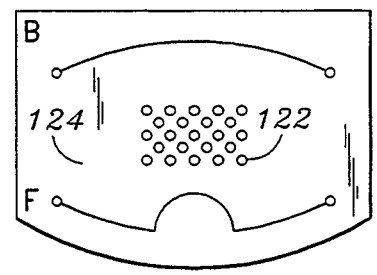

The devices of FIGS. 9 and 10 may be further modified as illustrated in FIGS. 11 and 12. A device 110 (FIG. 11) is generally similar to the device 90 but includes a plurality of openings or holes 112 formed in a central portion 114. A device 120 in FIG. 12 is similar to the device 100 but includes a plurality of openings or holes 122 in a central portion 124. The holes 112 and 122 are typically smaller than the fecal mass that may be deposited onto the device 110 or 120 when in use, such that all or substantially all of the fecal mass will be retained on the device 110 or 120. The holes 112, 122 help to drain unwanted fluid such as urine which may be inadvertently collected in the central portion, further avoiding contamination of the fecal specimen.

Although the devices illustrated in FIGS. 1–12 are generally rectangular, other shapes may also be used, such as elliptical or oval shapes. In such instances, the overall longer dimension of the device and the lengths of the slits are as described above with respect to the device 20.

Figure 13:
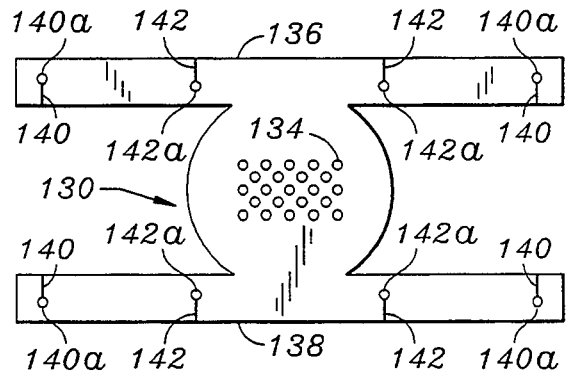
FIG. 13 is a top view of another embodiment of a device in accordance with the present invention.
Figure 14:
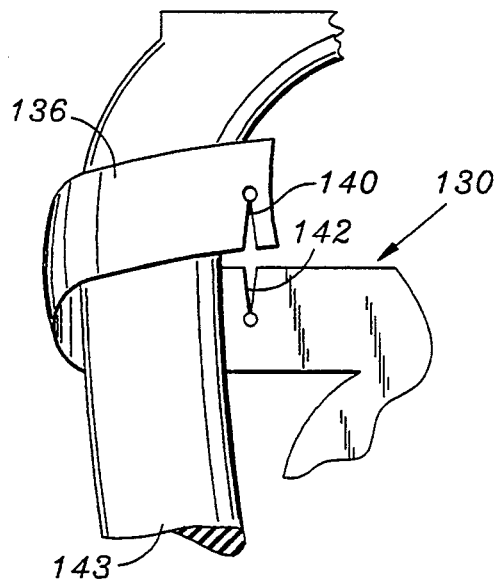
FIG. 14 is a partial view of the device of FIG. 13 as it is installed onto a toilet seat.

Turning now to FIGS. 13 and 14, another embodiment of a device in accordance with the present invention is illustrated. Such a device 130 includes a central portion 132 having a plurality of small openings 134. Integrally formed generally parallel straps 136, 138 are formed at opposite peripheral portions of the central portion 132. Each of the straps includes two pairs of slits 140, 142 with end eyes or holes 140a, 142a. The slits 140 are formed proximate the outer end of the straps 136, 138 and the slits 142 are formed on the opposite edge of the straps 136, 138 near the central portion 132.

In use, the device 130 is placed beneath a toilet seat between the seat and the bowl. The extensions of the straps 136, 138 are formed about the rim of the seat and are secured by joining the slits 140, 142. For example, one end of the strap 136 (FIG. 14) is brought around the outer edge of the rim of the toilet seat 143 and over the seat 143. The slit 140 near such end of the strap 136 is joined to the slit 142 nearest the same end of strip 136, forming a loop around the toilet seat. Similarly, the other strap ends are formed about the toilet seat and joined by respective slits 140, 142, forming a total of four loops that suspend the device 130 from the toilet seat 143. Thus, the central portion 132 is suspended below the seat but above the surface of the water contained within the bowl. Once a fecal specimen is deposited on the central portion 132 and suitable samples are collected, the loops formed by the straps are either easily torn or the slits 140, 142 are disengaged and the device including the remainder of the fecal specimen is lowered into the bowl for easy, clean disposal. The openings 134, as with the openings 112, 122, provide a means for draining unwanted fluids such as urine from the central portion 132. However, the device 130 may also be formed without the openings 134 if desired.

The device 130 is formed from a single piece of single or multiple layer paper or paper-like material of sufficient strength and stiffness for the straps 136, 138 to be looped and joined as described above. For example, the device 130 may be formed from multi-layered filter paper that is strengthened and stiffened by overcoating with resin, lacquer, or a polymeric material. If desired, only the straps 136, 138 of the device 130 may be overcoated to give the straps 136, 138 the desired additional strength and stiffness, while leaving the remainder of the device 130, such as the central portion 132, relatively flexible but of sufficient strength for successful sample collection. As an alternative, the device 130 may be formed from paper manufactured with binders, such as carboxymethyl cellulose, hydroxyethyl cellulose, methyl cellulose, or the like, to impart the desired strength and stiffness. As a further alternative, portions of the device may be formed from different materials and then joined together to form the completed device. For example, a first relatively stronger, stiffened material may be used for the straps 136, 138, and a second, relatively less strong and more flexible material, such as single or multi-layered filter paper, may be used for the central portion 132.

Figure 15:
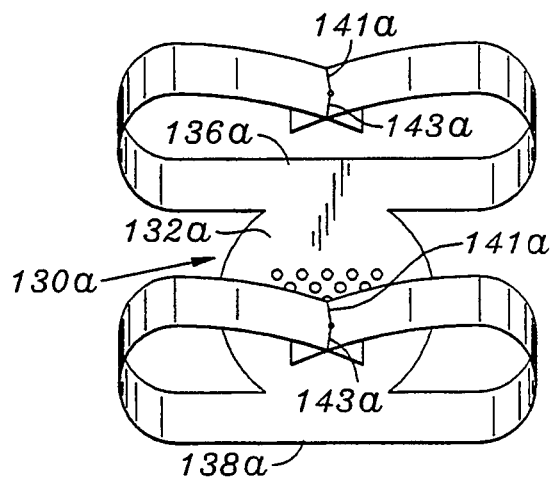
FIG. 15 is another embodiment of the device of FIG. 13.

The device 130 may be modified as illustrated in FIG. 15. Such a device 130A is similar to the device 130 and includes straps 136A, 138A. Slits 141A, 143A are formed in opposite ends of the straps 136A, 138A. The straps 136A, 138A are long enough such that when, for example, the slits 141A, 143A are joined in the opposite ends of the strap 136A, the resulting loop is of a size sufficient to fit over the width of a toilet seat. The strap 138A is similarly sized. Thus, the straps 136A, 138A may be formed into two large loops as illustrated in FIG. 15 and the device 130A then installed over a toilet seat, with the ends of the loops 136A, 138A above the seat and a central portion 132A of the device 130A suspended below the seat but above the water line within the toilet bowl.

Figure 16:
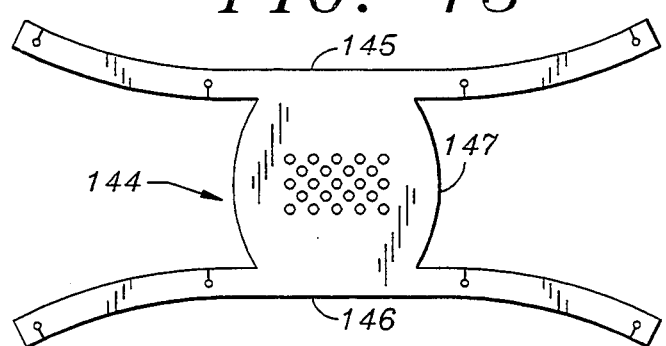
FIG. 16 is a top view of a modified form of the device of FIG. 13.

With reference to FIG. 16, a device 144 is similar to the device 130 but includes outwardly curved straps 145, 146 and a slightly broadened central portion 147. The device 144 is used in a fashion similar to that of the device 130.

Figure 17:
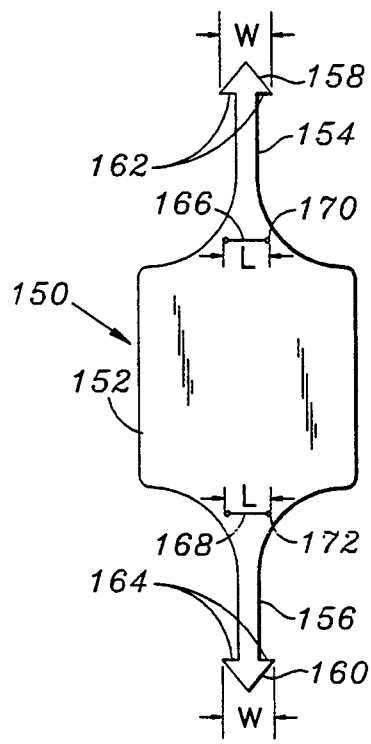
FIG. 17 is a top view of another embodiment of a device in accordance with the present invention.

Turning to FIG. 17, a device 150 in accordance with the present invention includes a generally rectangular center portion 152. Two elongated arms or straps 154, 156 are formed at opposite ends of the central portion 152. The ends 158, 160 of the straps 154, 156 are formed in the shape of arrowheads, including shoulders 162, 164. Two slits, 166, 168 are formed generally at the base area of the straps 154, 156, respectively, and each include stress distribution end eyes or holes 170, 172. The overall width "W" of the base of the ends 158, 160 at the shoulders 162, 164 is greater than the overall length "L" of the slits 166, 168 and holes 170, 172.

Figure 18:
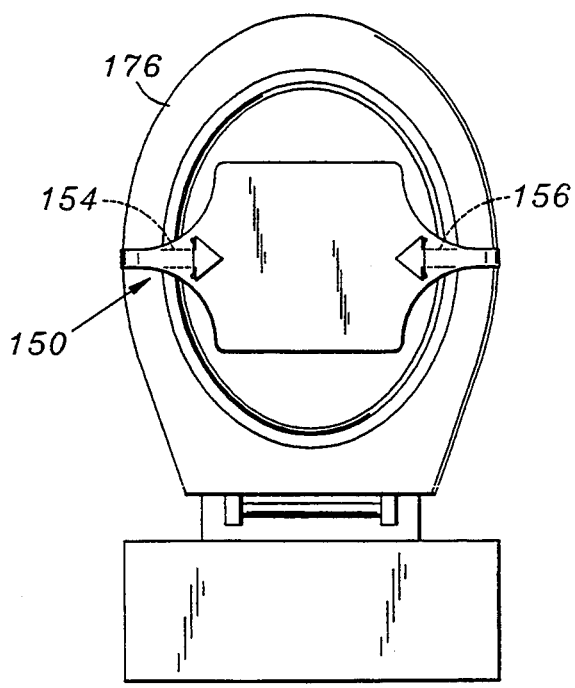
FIG. 18 is a top view of the device of FIG. 15 installed on a toilet seat.

To install the device 150 on a toilet seat, the device 150 is laid over the top of a toilet seat 176 as illustrated in FIG. 18 with the straps 154, 156 draped over the edge of the seat 176. The seat 176 is lifted slightly. While holding the device 150 in place, the strap 154 is looped around the rim of the seat 176 and the arrowhead-shaped end 158 is inserted through the slit 166 with the shoulders 162, 164 of end 158 retained within the slit 166. Similarly, the strap 156 is looped around the rim of the toilet seat 176. The device 150 thus is suspended from the toilet seat 176 with the center portion below the top of the seat 176. After the sample is collected as has been described above with respect to the other embodiments, the straps 154, 156 may, for example, be easily torn and the device 150 with the remaining specimen lowered into the toilet bowl for sanitary disposal.

The device 150 may be made from a single piece of single or multiple layer paper or paper-like material such as that described above with respect to the device 130. The entire device 150 may be formed from material of sufficient strength and stiffness for the straps 154, 156 to be looped and secured within the slits 168, 170 as described above, or the straps 154, 156 may be formed of such material with the central portion being formed from relatively less strong and more flexible material in a manner as described above respect to the device 130.

The device 150 may also include openings or holes in the central portion similar to the openings or holes 112, 122 and 134.

Although the embodiments of the device of the present invention as described above are formed from a paper-like material that may be disposed of directly in the toilet, each of the embodiments described may also be formed from polyester or other plastic sheet material, as well as woven synthetic material and nonwoven (matted or randomly oriented) synthetic fibers. In such an instance, the device would be installed onto the toilet seat as described above. Once the specimen is collected and the sample taken, the device is torn or cut or, in the embodiments of FIGS. 13-16, one or more loops that suspend the device from the toilet seat may be opened, the remaining fecal mass is dropped into the toilet bowl and disposed of, and the device itself is removed from the seat and disposed of in a suitable, preferably closed, container. Such a device formed from a plastic or other synthetic material is inexpensive and easy to use.

Thus, a device in accordance with the present invention is easily and inexpensively manufactured, is easily used by a patient to collect fecal samples and specimens and may be disposed of cleanly and efficiently by the patient. The device may be folded into a very thin package for economical shipping to the patient.

The device of the present invention is not to be limited to the embodiments disclosed herein but is to be given the full scope of the appended claims including all equivalents thereto.

We claim:

1. A fecal specimen collection device for use on a conventional toilet seat which is pivotally attached on a toilet bowl, the seat having an upper and lower surface bounded by opposite user support sides each having an outer peripheral edge and having an opening extending through said surfaces for passage of waste matter, the device including a sheet of flexible non-rigid material having first and second opposite edges and third and fourth opposite edges, the sheet including not more than a single lengthwise portion running from the first edge to the second edge, the lengthwise portion being free of openings and cuts, and straps on either side of the lengthwise portion defined by slits in the sheet, the slits separating the lengthwise portion from the straps and being generally parallel to and proximate the third and fourth opposite edges of the sheet, the slits having a length such that the outer peripheral edges of the seat can pass through said slits thus positioning one strap across the upper surface of the seat near the pivotal attachment and the other strap across the upper surface at a front of the seat with the single lengthwise portion of the sheet disposed with at least a portion thereof below the lower surface and extending across said opening so as to retain fecal matter deposited thereon by a user, the sheet being of such a thickness and consistency such that the straps may be easily torn subsequent to deposition of said fecal matter whereby the device can be lowered into the toilet bowl for disposal.

2. A device as in claim 1 wherein the material has a thickness not greater than 0.0055 inch.

3. A device as in claim 2 wherein the material has a thickness not greater than 0.002 inch.

4. A device as in claim 2 wherein the device is made of tissue-like cellulose paper.

5. A device as in claim 1 wherein the sheet is rectangular.

6. A device as in claim 5 wherein the material is paper.

7. A device as in claim 5 wherein the material is a plastic substance.

8. A device as in claim 1 wherein both slits are curved.

9. A device as in claim 8 wherein the slits are curved toward each other.

10. A device as in claim 8 wherein the slits are curved away from each other.

* * * * *